United States Patent [19]

Littel-van den Hurk et al.

[11] Patent Number: 5,951,988
[45] Date of Patent: Sep. 14, 1999

[54] ADJUVANT FORMULATION WITH ENHANCED IMMUNOGENIC ACTIVITY, AND RELATED COMPOSITIONS AND METHODS

[75] Inventors: Sylvia van Drunen Littel-van den Hurk, Saskatoon, Canada; Timothy Zamb, Setauket, N.Y.; Mark J. Redmond, Saskatoon, Canada

[73] Assignee: University of Saskatchewan, Saskatoon, Canada

[21] Appl. No.: 08/463,837

[22] Filed: Jun. 5, 1995

Related U.S. Application Data

[63] Continuation of application No. 08/039,990, Mar. 30, 1993, abandoned.

[51] Int. Cl.$^6$ .......................... A61K 39/00; A61K 45/00
[52] U.S. Cl. ..................... 424/278.1; 424/184.1; 424/204.1; 424/234.1; 424/283.1; 514/642
[58] Field of Search .............................. 424/184.1, 204.1, 424/234.1, 278.1, 283.1; 514/642

[56] References Cited

U.S. PATENT DOCUMENTS

| | | | |
|---|---|---|---|
| 4,384,974 | 5/1983 | Guthauser | 252/309 |
| 4,395,394 | 7/1983 | Wolff, III et al. | 424/88 |

OTHER PUBLICATIONS

D. Gall, "The Adjuvant Activity of Aliphatic Nitrogenous Bases", *Immunology* 11:369–386 (1966).
A. C. Allison, "Mode of Action of Immunological Adjuvants", *J. Reticuloendothel Soc.* 26:619–630 (1979).
Snippe et al., "Adjuvanticity of Dimethyl Dioctadecyl Ammonium Bromide in Guinea Pigs", *Int. Archs Allergy appl. Immun.* 68:201–208 (1982).
Smith et al., "Cyclophosphamide and dimethyl dioctadecyl ammonium bromide immunopotentiate the delayed–type hypersensitivity response to inactivated enveloped viruses", *Immunology* 58:245–250 (1986).
Ziola et al., "In vitro proliferation of lymphocytes from cyclophosphamide–pretreated mice immunized with antigen mixed with dimethyl dioctadecyl ammonium bromide", *Journal of Immunological Methods* 97:159–164 (1987).
Babiuk et al., "Protection of Cattle from Bovine Herpesvirus Type 1 (BHV–1) Infection by Immunization with Individual Viral Glycoproteins", *Virology* 159:57–66 (1987).
van Dalen et al., "Preparation and Characterization of Liposomes with Incorporated *Neisseria gonorrhoeae* Protein IB Amphiphilic Adjuvants", *Journal of Controlled Release* 7:123–132 (1988).
Limpens et al., "Synergistic effects of locally administered cytostatic drugs and a surfactant on the development of delayed–type hypersensitivity to keyhole limpet haemocyanin in mice", *Clin. exp. Immunol.* 78:256–262 (1989).
Felgner, "Particulate systems and polymers for in vitro and in vivo delivery of polynucleotides", *Advanced Drug Delivery Reviews* 5:163–187 (1990).
*Kodak Laboratory Chemicals Bulletin*, vol. 56, No. 1, 1985.
Fed. Registr. 55(219):47322–3, Nov. 13, 1990. "Indirect Food Additives; adjuvants, production".
Hunter et al. in "Immunological Adjuvants and Vaccines". Ed. Gregoriadis et al, Plenum Publishing Corp., 1989, pp. 133–144.
Byars et al. Vaccine, 1987, vol. 5, pp. 223–228.
Davis et al. Encyclopedia of Emulsion Technology, 1985, vol. 2, Ed. Becher, Marcus–Decker Inc., New York, pp. 159–237.

*Primary Examiner*—Ponnathapura Achutamurthy
*Attorney, Agent, or Firm*—Robins & Associates

[57] ABSTRACT

Adjuvant formulations are provided containing quaternary ammonium salts in conjunction with an oil component which may be a mineral oil, an animal oil, a vegetable oil, a mixture thereof, or an oil-in-water emulsion of one or more of such oils. These formulations are useful in conjunction with known immunological substances, e.g., viral or bacterial antigens in a vaccine composition, in order to enhance the immunogenic response. The compositions are also useful without an incorporated antigen as nonspecific immunostimulatory formulations.

25 Claims, No Drawings

ADJUVANT FORMULATION WITH ENHANCED IMMUNOGENIC ACTIVITY, AND RELATED COMPOSITIONS AND METHODS

This application is a continuation of U.S. patent application Ser. No. 08/039,990, filed Mar. 30, 1993 now abandoned.

TECHNICAL FIELD

The present invention relates generally to agents which enhance the immune response to a particular antigen, and more specifically relates to novel adjuvant formulations having enhanced immunogenic activity. The invention additionally relates to vaccine compositions containing the novel adjuvant formulations, and to methods for making and using the compositions of the invention.

BACKGROUND

As is well-known in the field of immunology, "adjuvants" are agents which act in a nonspecific manner to increase an immune response to a particular antigen, thus reducing the quantity of antigen necessary in any given vaccine, as well as the frequency of injection. See, e.g., A. C. Allison, *J. Reticuloendothel. Soc.* 26:619–630 (1979). A number of aliphatic nitrogenous bases have been proposed for use as immunologic adjuvants, including amines, quaternary ammonium compounds, guanidines, benzamidines and thiouroniums (D. Gall, *Immunology* 11:369–386 (1966)). Specific such compounds include dimethyldioctadecylammonium bromide (DDA) (available from Kodak) and N,N-dioctadecyl-N,N-bis(2-hydroxyethyl)propanediamine ("avridine"). The use of DDA as an immunologic adjuvant has in fact been widely publicized; see, e.g., the Kodak Laboratory Chemicals Bulletin 56(1):1–5 (1986); *Adv. Drug Deliv. Rev.* 5(3):163–187 (1990); *J. Controlled Release* 7:123–132 (1988); *Clin. Exp. Immunol.* 78(2):256–262 (1989); *J. Immunol. Methods* 97(2):159–164 (1987); *Immunology* 58(2):245–250 (1986); and *Int. Arch. Allergy Appl. Immunol.* 68(3):201–208 (1982). Avridine, also, is well-known as an adjuvant. See, e.g., U.S. Pat. No. 4,310,550 to Wolff, III et al., which describes the use of N,N-higher alkyl-N',N'-bis(2-hydroxyethyl)propane diamines in general, and avridine in particular, as vaccine adjuvants. U.S. Pat. No. 5,151,267 to Babiuk and Babiuk et al., *Virology* 159:57–66 (1986), also relate to the use of avridine as a vaccine adjuvant. The foregoing references, as well as all other patents, patent applications, and publications cited herein, are hereby incorporated by reference in their entirety.

The present invention is directed to a technique whereby the immunogenic activity of compounds such as those identified above is enhanced. The technique involves admixture of an aliphatic nitrogenous compound such as DDA or avridine with a mineral oil, a vegetable oil, an animal oil, or a mixture thereof. Like the aforementioned nitrogenous compounds, certain oils have also been recognized to have adjuvant activity (see, e.g., U.S. Pat. Nos. 4,310,550, 4,395,394, 4,806,352, 4,867,899, 4,876,094 and 5,102,660). However, the inventors herein have found, surprisingly, that combining the selected nitrogenous compound with one or more such oils provides for superior adjuvant activity, far beyond the simple additive effect which would be expected upon combining the two types of adjuvants. Accordingly, then, the invention is primarily directed to methods and compositions which involve the combination of an aliphatic nitrogenous compound such as DDA or avridine with a selected oil as will be described in further detail below.

It has also been found, surprisingly, that the aforementioned compositions, containing an aliphatic nitrogenous compound and an oil component, have nonspecific immunostimulatory activity. Thus, the invention is also directed to a method for inducing an immune response in an individual by administering the composition of the invention without co-administration of an antigen, i.e., as a nonspecific immunostimulatory composition.

SUMMARY OF THE INVENTION

It is thus a primary object of the invention to provide a novel adjuvant formulation having enhanced immunogenic activity.

It is another object of the invention to provide such a formulation containing an aliphatic nitrogenous compound in the form of a quaternary ammonium salt as will be defined below and an oil selected from the group consisting of vegetable oils, mineral oil, animal oils, and mixtures thereof.

It is still another object of the invention to provide novel vaccines containing the aforementioned adjuvant formulation.

It is a further object of the invention to provide a method for producing an enhanced immune response in a vertebrate subject, involving administering a vaccine composition containing the novel adjuvant formulation.

It is yet a further object of the invention to provide a method for inducing an immune response, comprising administering the adjuvant formulation of the invention without an antigen, i.e., as a nonspecific immunostimulatory composition.

It is still a further object of the invention to provide a method for preparing the adjuvant formulation of the invention.

Additional objects, advantages and novel features of the invention will be set forth in part in the description which follows, and in part will become apparent to those skilled in the art upon examination of the following, or may be learned by practice of the invention.

In one aspect, then, the invention provides an adjuvant formulation consisting essentially of: (a) a quaternary ammonium salt having the structural formula

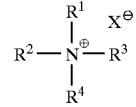

wherein $R^1$ and $R^2$ are independently selected from the group consisting of saturated hydrocarbon chains containing at least twelve carbon atoms, $R^3$ and $R^4$ are independently selected from lower alkyl groups, either unsubstituted or substituted with one to four substituents selected from the group consisting of hydroxyl and primary amino, and X is a halogen atom; and (b) an oil component comprising (i) an oil or (ii) an oil-in-water emulsion, wherein the oil in either (i) or (ii) is selected from the group consisting of mineral oil, vegetable oils, animal oils, and mixtures thereof.

In another aspect of the invention, vaccines are provided containing an antigen and an effective amount of the above-defined adjuvant formulation. The vaccine compositions may alternatively contain DNA, so as to be useful in DNA immunizations, in which case the adjuvant formulation acts to enhance the activity of antigens produced in vivo. In a related aspect, a method is provided for producing an enhanced immune response in a vertebrate subject, comprising administering a vaccine composition containing an antigen and an effective amount of the presently disclosed and claimed adjuvant formulation.

In still another aspect of the invention, a method is provided for inducing an immune response in a vertebrate subject, the method comprising administering the above-described formulation, containing a quaternary ammonium salt and an oil component, without co-administration of an antigen.

In a further aspect of the invention, a method is provided for preparing an adjuvant formulation having enhanced immunogenic activity, which involves dissolving the selected quaternary ammonium salt in a compatible solvent, admixing therewith a selected oil component comprising a mineral oil, a vegetable oil, an animal oil, or a mixture thereof, and incorporating a biological buffer to provide the adjuvant formulation with a pH in the physiological range. Alternatively, and preferably, the solvent is omitted, and the selected quaternary ammonium salt is dissolved directly into the oil component at a slightly elevated temperature. In this way, the final adjuvant formulation is completely free of solvent.

DETAILED DESCRIPTION OF THE INVENTION

Definitions and nomenclature

Before the present compositions and methods are disclosed and described, it is to be understood that this invention is not limited to specific quaternary ammonium salts, specific oils, or to specific antigens, as such may vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a quaternary ammonium salt" includes mixtures of such salts, reference to "an oil" includes mixtures of two or more oils, and the like.

By the term "alkyl" as used herein is meant a branched or unbranched saturated hydrocarbon chain of 1 to 20 carbon atoms. The term "lower alkyl" intends an alkyl group of 1 to 6 carbon atoms such as methyl, ethyl, n-propyl, isopropyl, t-butyl, and the like.

The term "aliphatic" is also used in its conventional sense to mean a, saturated, linear hydrocarbon chain. "Lower aliphatic" intends an aliphatic group of 1 to 6 carbon atoms.

"Halogen" intends an atom which is bromine, chlorine, fluorine or iodine. The preferred halogen atom contained within the presently disclosed quaternary ammonium salts is bromine.

An "antigen" refers to a molecule containing one or more epitopes that will stimulate a host's immune system to make a humoral and/or cellular antigen-specific response. The term is used interchangeably with the term "immunogen." It will also be appreciated by those skilled in the art that the adjuvant formulations of the invention may be used to enhance the activity of antigens produced in vivo, i.e., in conjunction with DNA immunization.

An "immunological response" to an antigen or vaccine is the development in the host of a cellular and/or antibody-mediated immune response to the composition or vaccine of interest. Usually, such a response includes but is not limited to one or more of the following effects; the production of antibodies, B cells, helper T cells, suppressor T cells, and/or cytotoxic T cells and/or γδT cells, directed specifically to an antigen or antigens included in the composition or vaccine of interest.

By "vertebrate subject" is meant any member of the subphylum chordata, including, without limitation, mammals such as cattle, sheep, pigs, goats, horses, and man; domestic animals such as dogs and cats; and birds, including domestic, wild and game birds such as cocks and hens including chickens, turkeys and other gallinaceous birds. The term does not denote a particular age. Thus, both adult and newborn animals are intended to be covered.

By "pharmaceutically acceptable" or "pharmacologically acceptable" is meant a material which is not biologically or otherwise undesirable, i.e., the material may be administered to an individual along with the selected adjuvant formulation without causing any undesirable biological effects or interacting in a deleterious manner with any of the components of the vaccine composition in which it is contained.

By "physiological pH" or a "pH in the physiological range" is meant a pH in the range of approximately 7.2 to 8.0 inclusive, more typically in the range of approximately 7.2 to 7.6 inclusive.

The adjuvant formulation of the invention thus comprises a quaternary ammonium salt as described above in combination with an oil component.

Preferred quaternary ammonium salts are wherein the substituents $R^1$ and $R^2$ are alkyl of twelve to twenty carbon atoms, and $R^3$ and $R^4$ are lower alkyl. For example, when the selected quaternary ammonium salt is DDA, $R^1$ and $R^2$ are each —$C_{18}H_{37}$, $R^3$ and R4 are each methyl, and X is bromine.

The oil component, as noted earlier, may be either a single oil, a mixture of oils, or an oil-in-water emulsion. The oil may be a mineral oil, a vegetable oil, or an animal oil. Mineral oil or oil-in-water emulsions in which the oil component is mineral oil are preferred.

By "mineral oil" is meant that mixture of liquid hydrocarbons obtained from petrolatum via a distillation technique; the term is synonymous with "liquid paraffin", "liquid petrolatum" and "white mineral oil." The term is also intended to include "light mineral oil," i.e., an oil which is similarly obtained by distillation of petrolatum, but which has a slightly lower specific gravity than white mineral oil. See, e.g., *Remington's Pharmaceutical Sciences*, 18th Edition (Easton, Pa.: Mack Publishing Company, 1990), at pages 788 and 1323. A particularly preferred oil component for use in conjunction with the present formulations is the oil-in-water emulsion (comprising a light mineral oil as well as 0.05% formalin, and 30 mcg/ml gentamicin as preservatives) available as EMULSIGEN PLUS™ from MVP Laboratories, Ralston, Neb.

"Animal oils" include, for example, cod liver oil, halibut oil, menhaden oil, orange roughy oil and shark liver oil, all of which are available commercially.

Vegetable oils, including canola oil, almond oil, cottonseed oil, corn oil, olive oil, peanut oil, safflower oil, sesame oil, soybean oil, and the like, may also be used.

In one embodiment, the adjuvant formulations of the invention contain a solvent for the quaternary ammonium salt, an emulsifier, and a biological buffer effective to provide the formulation with a pH in the physiological range. Typical solvents include lower alkanols such as ethanol, isopropanol and butanol. It is not essential, however, that a solvent be included in the formulations, in that the composition may if desired be prepared by dissolving the quaternary ammonium salt in the oil component at a slightly elevated temperature, (typically greater than or equal to about 70° C.), obviating the need for a solvent.

Compounds which may serve as emulsifiers herein include natural and synthetic emulsifying agents, as well as anionic, cationic and nonionic such compounds. Among the synthetic compounds, anionic emulsifying agents include, for example, the potassium, sodium and ammonium salts of lauric and oleic acid, the calcium, magnesium and aluminum salts of fatty acids (i.e., metallic soaps), and organic sulfonates such as sodium lauryl sulfate. Synthetic cationic agents include, for example, cetyltrimethylammonium bromide, while synthetic nonionic agents are exemplified by glyceryl esters (e.g., glyceryl monostearate), polyoxyethylene glycol esters and ethers, and the sorbitan fatty acid esters (e.g., sorbitan monopalmitate) and their polyoxyethylene derivatives (e.g., polyoxyethylene sorbitan monopalmitate). Natural emulsifying agents include acacia, gelatin, lecithin and cholesterol.

For the biological buffer, virtually any solution may be used which is pharmacologically acceptable and which provides the adjuvant formulation with the desired pH, i.e., a pH in the physiological range. Examples of buffer solutions include saline, phosphate buffered saline, Tris buffered saline, Hank's buffered saline, growth media such as Eagle's Minimum Essential Medium ("MEM"), and the like.

Preferred relative amounts of the various formulation components are as follows. Most preferably, the adjuvant formulation will contain on the order of 5 to 15 mg quaternary ammonium salt per 1 ml formulation. The oil component will preferably represent about 10% to 60% (v/v) of the formulation, while the solvent, if present, will preferably represent about 5% to 15% (v/v) of the formulation and the emulsifier will represent about 0.5% to 1.5% (v/v) of the formulation. The biological buffer will be present in an amount sufficient to give rise to the aforementioned relative quantities, and again, is such that a pH in the physiological range is provided.

The adjuvant formulations of the invention may be used for those purposes as presently known adjuvants; see, for example, "Immunological Adjuvants", World Health organization Technical Report Series, No. 595. For example, the formulations are useful when used in conjunction with vaccines such as, but not limited to, those for treating bovine respiratory disease ("Shipping Fever"), neonatal diarrhea, and the like. The antigens which may be incorporated into the present formulations include viral, prokaryotic and eukaryotic antigens, including but not limited to antigens derived from bacteria, fungi, protozoans and parasites. Preferred viral antigens include Rotaviruses, Herpes viruses, Corona viruses, Respiratory Synctial virus, Parainfluenza virus, Adenovirus, Pox viruses, Bovine herpes virus Type I, Bovine viral diarrhea virus, Bovine rotaviruses, and the like, while preferred bacterial antigens include those derived from Pasteurella, Actinobacillus, Haemophilus, and the like.

Vaccine compositions prepared with the present adjuvant formulation will typically contain on the order of 0.1 μg to 1000 μg, more preferably 1 μg to 100 μg, of the selected antigen, and on the order of 0.1 mg to 1000 mg, more preferably 1 mg to 100 mg, of the adjuvant formulation. The vaccine composition may additionally contain biological buffers, excipients, preservatives, and the like. Also, as noted above, the formulations may be administered without an antigen, so as to induce a nonspecific immunostimulatory response.

The vaccine is then administered to the selected individual in the manner conventional for the particular vaccine, generally as a single unit dose of an antigen in buffered saline, combined with the adjuvant formulation, administered enterally or parenterally, e.g., subcutaneously, intramuscularly, intradermally, intravenously, intraarterially, intraperitoneally, intranasally, orally, etc. Subcutaneous or intramuscular injection is, however, preferred. Preferably this initial dose is then followed, typically one to several weeks later, by further vaccinations.

The adjuvant formulations are typically prepared by dissolving the quaternary ammonium salt in a selected solvent, e.g., ethanol, isopropanol or butanol, as noted earlier herein, followed by incorporation of the oil component and any other components, e.g., preservatives, excipients, etc. Alternatively, the quaternary ammonium salt may be dissolved directly in the oil component, typically at temperatures greater than or equal to about 70° C., such that a solvent may be omitted.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

Experimental

The practice of the present invention will employ, unless otherwise indicated, conventional techniques of molecular biology, microbiology, virology, recombinant DNA technology, and immunology, which are within the skill of the art. Such techniques are explained fully in the literature. See, e.g., Sambrook, Fritsch & Maniatis, *Molecular Cloning: A Laboratory Manual,* Second Edition (1989); *DNA Cloning,* Vols. I and II (D. N. Glover, ed., 1985); *Oligonucleotide Synthesis* (M. J. Gait, ed., 1984); *Nucleic Acid Hybridization* (B. D. Hames & S. J. Higgins, eds., 1984); *Animal Cell Culture* (R. K. Freshney, ed., 1986); *Immobilized Cells and Enzymes* (IRL press, 1986); Perbal, B., *A Practical Guide to Molecular Cloning* (1984); the series, *Methods In Enzymology* (S. Colowick and N. Kaplan, eds., Academic Press, Inc.); and *Handbook of Experimental Immunology,* Vols. I–IV (D. M. Weir and C. C. Blackwell, eds., 1986, Blackwell Scientific Publications).

EXAMPLE 1

Preparation of DDA/Oil Adjuvant Formulation

Dimethyldioctadecyl ammonium bromide (DDA) was obtained from Kodak (Rochester, N.Y.) and EMULSIGEN PLUS™ was obtained from MVP Laboratories (Ralston, Neb.). All other reagents were of laboratory grade and are readily available from supply houses such as Sigma.

The adjuvant composition was formulated on the basis of a 15 mg DDA/animal dose. 150 mg of DDA were dissolved in 1 ml of absolute ethanol. The solution process required the warming of the reagents to approximately 30° C. A 90 μl volume of polyoxyethylene(20)sorbitan monooleate (TWEEN® 80, obtained from Aldrich Chemical Company) was added to the DDA-in-ethanol solution and mixed by vortexing for 0.5–1.0 minutes. EMULSIGEN PLUS™, 5.9 mls, was then added to equal 60% (v/v) of the final adjuvant preparation, and mixed thoroughly. The final volume was brought up to 10 mls using Tris buffered saline, pH 7.2. The dose of DDA/animal (15 mg) was contained in 1 ml of this adjuvant formulation.

EXAMPLE 2

Preparation and Evaluation of a Vaccine Containing the Novel Adjuvant Formulation (a.) Preparation of BHV-1 gIV Antigen:

The BHV-1 gIV subunit vaccine was prepared as described in co-pending, commonly assigned U.S. patent application Ser. No. 07/921,849, now U.S. Pat. No. 5,585,264, incorporated herein by reference. Briefly, the antigen consisted of recombinant gIV modified to be secreted by a vaccinia virus expression vector. BSC-1 cells (ATCC Cat. No. CCL-26) were cultured in MEM containing 10% fetal bovine serum. Confluent monolayers in serum-free MEM were infected at a multiplicity of infection of 0.1 with the recombinant vaccinia virus containing the modified gene for BHV-1 gIV (Truncated gIV). 72 hours after infection or at the appearance of total cellular cytopathy, the recombinant gIV was harvested by collecting the media from the culture flasks. Cell debris was removed by centrifugation at 1000 g for 20 min. The medium was filtered through a 0.45 μm filter, and the detergents NONIDET® P40 and sodium deoxycholate were added to the filtrate to final concentrations of 0.1%. The truncated gIV was then affinity purified by chromatography using the method described by van Drunen Littel-van den Hurk (1985) *Virology* 144:204–215. Doses of truncated gIV used in the trials ranged from 2.5 to 25 μg. The vaccines were prepared by mixing the antigen in 1 ml of Tris buffered saline, pH 7.2, with 1 ml of the adjuvant formulation.

(b.) Immunological Analysis:

To measure the immune response to the vaccine formulations, the serum from test animals was screened by an ELISA using gIV as the antigen. This assay was performed essentially as described previously by van Drunen Littel-van den Hurk (1985) *Virology* 441:204–215 and (1984) *Virology* 135:466–479.

Test Species: Bovine (8 animals/group)
Antigen: truncated gIV
Dose: 25 μg/animal Animals were immunized twice with a vaccine formulation consisting of truncated gIV adjuvanted with the formulation prepared in Example 1, EMULSIGEN PLUS® or avridine (synthesized by and obtained from Pharm-eco Labs, Lexington Mass.).

The vaccines were prepared by mixing the antigen in 1 ml of Tris buffered saline, pH 7.2, with 1 ml of the adjuvant formulation. To prepare avridine, (N,N-dioctadecyl-N',N'-bis(2-hydroxyethyl-)propanediamine), 150 mg of the chemical was dissolved in 1 ml of absolute ethanol and then combined with 90 μl of TWEEN® 80 by thorough mixing. Next, 4.7 ml of INTRALIPID® (obtained from Riker) were combined with the avridine/ethanol/TWEEN® 80 solution and mixed thoroughly by vortexing. 4.0 mls of saline were added to the solution to complete the adjuvant preparation. The vaccine was prepared by mixing antigen and adjuvant solutions such that each animal received 15 mg of avridine in a 2 ml volume.

To prepare the EMULSIGEN PLUS™ formulated vaccines, truncated gIV was mixed with adjuvant to produce a vaccine containing 30% (v/v) EMULSIGEN PLUS™/dose. The remaining volume of vaccine was made up with a biological buffer.

Assay results were as set forth in Table 1:

TABLE 1

ANTI gIV ELISA RESULTS

| Adjuvant | Geometric Mean Titre | | |
|---|---|---|---|
| | Day 1 | Day 21 | Day 35 |
| Avridine | <100 | 380 | $4.9 \times 10^4$ |
| EMULSIGEN PLUS ™ | <100 | 56 | 5120 |
| Ex. 1 Formulation | <100 | 250 | $7.3 \times 10^4$ |

The results of the trial indicated that the formulation of the invention was superior to either avridine or EMULSIGEN PLUS™.

EXAMPLE 3
Effect on Immune Response of Amine Salt Concentration

An adjuvant formulation was prepared as described in Example 1 above, with the exception that concentration of DDA was adjusted to 5, 15 or 45 mg/ml of adjuvant. The adjuvant formulation concentration of EMULSIGEN PLUS™ was fixed at 60%, and the emulsifier was again TWEEN® 80. The vaccines were formulated by mixing 1 ml of adjuvant with 1 ml of Tris buffered saline, pH 7.2, containing the 2.5 μg of truncated gIV.

Test Species: Rabbit (4 animals/group).
Assay results are set forth in Table 2.

TABLE 2

ANTI gIV ELISA RESULTS

| DDA | Geometric Mean Titre | | | |
|---|---|---|---|---|
| mg/dose | Day 1 | Day 14 | Day 28 | Day 35 |
| 5 | <10 | 5120 | 2560 | 163800 |
| 15 | <10 | 3620 | 3620 | 163800 |
| 45 | <10 | 1280 | 1810 | 40960 |

The trial indicated that the optimized DDA concentration is between approximately 5 and 15 mg/dose.

EXAMPLE 4
Effect on Immune Response of Oil Concentration

An adjuvant formulation was prepared as described in Example 1 above, with the exception that the volume of EMULSIGEN PLUS™ was adjusted to yield formulations containing 60, 30 and 10% (v/v). The DDA concentration was fixed at 15 mg/dose DDA. The vaccines were formulated by mixing 1 ml of adjuvant with 1 ml of Tris buffered saline, pH 7.2, containing the 2.5 μg of truncated gIV.

Test Species: Rabbit (4 animals/group).
Assay results are set forth in Table 3.

TABLE 3

ANTI gIV ELISA RESULTS

| Adjuvant % v/v | Geometric Mean Titre | | | |
|---|---|---|---|---|
| EMULSIGEN PLUS ™ | Day 1 | Day 14 | Day 28 | Day 35 |
| 0 | <10 | 80 | 113 | 7240 |
| 10 | <10 | 2560 | 1810 | 40966 |
| 30 | <10 | 2560 | 5120 | 40960 |
| 60 | <10 | 3620 | 3620 | 163800 |

The trial indicated that higher concentrations of EMULSIGEN PLUS™ are preferred, although not essential for some enhancement of the immunogenic response.

EXAMPLE 5
Effect on Immune Response of Oil Type

EMULSIGEN PLUS™ is composed of a light mineral oil and three emulsifiers. The present experiment was carried out to determine what other types of oils would be effective in the amine-containing adjuvant formulations of the invention. Accordingly, oils of animal, vegetable and mineral origin were evaluated in combination with DDA. Formulation proceeded as described in Example 1 above, with the exception that the EMULSIGEN PLUS™ was replaced with a volume of an alternative oil (60% v/v) and containing 1.5 mls of MONTANIDE® 80 (obtained from SEPPIC). The vaccines were formulated by mixing 1 ml of adjuvant with 1 ml of Tris buffered saline, pH 7.2, containing the 2.5 μg of truncated gIV.

Test Species: Rabbit (4 animals/group); all animals were immunized a second time, 21 days following initial immunization.

Assay results are set forth in Table 4.

TABLE 4

ANTI gIV ELISA RESULTS

| Oil | Geometric Mean Titre | | | |
|---|---|---|---|---|
|  | Day 1 | Day 14 | Day 28 | Day 35 |
| EMULSIGEN ™ | <10 | 3620 | 3620 | 163800 |
| Mineral[1] | <10 | 1810 | 1810 | 231698 |
| Vegetable[2] | <10 | 320 | 320 | 40960 |
| Animal[3] | <10 | 452 | 320 | 28963 |

[1]Light mineral oil, Emulsifier: MONTANIDE ® 80
[2]Canola oil, Emulsifier: MONTANIDE ® 80
[3]Cod liver oil, Emulsifier: MONTANIDE ® 80

The results indicate that any oil is suitable for combination with DDA, although mineral oil is preferred as it is most potent.

EXAMPLE 6

Effect on Immune Response of Solvent

This experiment substituted isopropanol as the alcohol for dissolving the DDA. Adjuvant formulation with this exception proceeded as described in Example 1. The vaccines were prepared by mixing 2.5 µg antigen of truncated gIV in 1 ml of Tris buffered saline, pH.7.2, with 1 ml of the adjuvant formulation.

Test Species: Rabbit (4 animals/group).
Assay results are set forth in Table 6.

TABLE 6

ANTI gIV ELISA RESULTS

|  | Day 1 | Day 14 | Day 28 | Day 35 |
|---|---|---|---|---|
| Ethanol | <10 | 3620 | 3620 | 163800 |
| Isopropanol | <10 | 3620 | 2560 | 327650 |

Results indicated that solvents other than ethanol are suitable for formulating the adjuvant.

EXAMPLE 7

Effect of dissolving DDA directly in oil

Three formulations were assessed using truncated gIV from BHV-1 as a model antigen system. The adjuvant formulations were VSA3 (emulsion+DDA), and formulations containing a vegetable oil and mineral oil with DDA. The components of the almond oil/DDA and mineral oil/DDA adjuvant are listed in Table 7. The formulations were made by mixing all components in the oil phase together in one container, and all components of the water phase together in another. Both the oil phase and water phase were heated to a temperature between 60–70° C., and then mixed using an industrial homogenizer. Emulsions were formed under positive pressure at 40 psi and the temperature in the emulsion maintained at 50–60° C. The emulsions were found to be homogenous with a particle size approximating 2 µm or less after 7.5 to 10 minutes of emulsification. The resulting formulations consisted of 30% oil with 15 mg of DDA per 1 ml. For injection, one dose was 1 ml of the required emulsion mixed with 1 ml of aqueous phase truncated gIV (40 µg/dose). The resulting 2 ml dose therefore contained 15% oil, 15 mg DDA, and 40 µg of truncated gIV.

Animals (5 per group) were immunized at Day 0, bled at Day 21 and Day 45. At Day 21, animals were given booster inoculum (gIV in the identical formulation with which they were immunized). Table 8 indicates the serum antibody response in cattle following immunization with gIV using either VSA3, the mineral oil DDA formulation or the almond oil/DDA formulation. Serum antibody titres were determined using enzyme linked immunosorbent assays (ELISA) or serum neutralizing antibody tests. Results are shown in Table 8.

TABLE 7

| Formulation | Almond Oil/DDA | Mineral Oil/DDA |
|---|---|---|
| Oil Phase | 30 g Almond Oil SR NF | 30 g Mineral Oil |
|  | 1.3 g Span 80 (Crill 4) | 1.3 g Span 80 |
|  | 1 g Tocopherol | 1 g Tocopherol |
|  | 1 mg Propylparaben | 1 mg Propylparaben |
|  | 1.5 g DDA | 1.5 g DDA |
| Water Phase | 1.7 g TWEEN 80 (Crillet 4) | 1.7 g Tween 80 |
|  | 64.5 g Distilled Water | 64.5 g Distilled Water |
|  | 10 mg Methylparaben | 10 mg Methylparaben |

TABLE 8

|  | Day 0 | | Day 21 | | Day 45 | |
|---|---|---|---|---|---|---|
| Formulation | gIV[(1)] | SN[(2)] | gIV | SN | gIV | SN |
| VSA3 | 0 | 0 | 1468 | 38 | 11746 | 1260 |
| Mineral Oil/DDA | 5 | 0 | 176 | 19 | 7131 | 1243 |
| Almond Oil/DDA | 6 | 0 | 97 | 89 | 879 | 282 |

[(1)]Anti-gIV titres were assessed using an Enzyme Linked Immunosorbent Assay
[(2)]Serum neutralization was assessed by the inhibition of BHV-1 into a bovine cell line

EXAMPLE 8

Efficacy of VSA3 used with bacterial antigens

The same formulations were assessed using a rabbit-leukotoxin model. Animals were immunized at Day 0, bled at Day 21 and boosted with the same antigen-adjuvant preparation and bled again at Day 45. Table 9 shows the results of the trial and indicates that all three adjuvants behaved in a similar way when used in this model.

TABLE 9

|  | Day 0 | Day 21 | Day 45 |
|---|---|---|---|
| VSA3 | 0 | 776 | 24833 |
| Mineral Oil/DDA | 0 | 3104 | 24833 |
| Almond Oil/DDA | 0 | 93104 | 24833 |

Anti-Leukotoxin titres were assessed by ELISA

We claim:

1. A method for preparing an adjuvant formulation having enhanced immunogenic activity, comprising:

(a) dissolving a selected quaternary ammonium salt in a compatible solvent at a temperature in the range of approximately 30° C. to 35° C., the salt having the structural formula

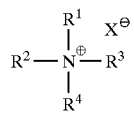

wherein $R^1$ and $R^2$ are independently selected from the group consisting of saturated hydrocarbon chains containing at least twelve carbon atoms, $R^3$ and $R^4$ are independently selected from lower alkyl groups, either unsubstituted or substituted with one to four substituents selected from the group consisting of hydroxyl and primary amino, and X is a halogen atom;

(b) admixing into the solution produced in step (a) an effective amount of a selected emulsifier and an oil component selected from the group consisting of a mineral oil, a vegetable oil, an animal oil, and mixtures thereof; and (c) incorporating into the solution a biological buffer effective to provide the adjuvant formulation with a pH in the physiological range, wherein the relative quantities of quaternary ammonium salt, solvent, emulsifier, oil component and buffer are such that the adjuvant formulation contains approximately 5 to 15 mg quaternary ammonium salt in 1 ml formulation, the oil component represents approximately 10% to 60% by volume of the formulation, the solvent represents approximately 5% to 15% by volume of the formulation, and the emulsifier represents approximately 0.5% to 1.5% by volume of the formulation, and further wherein the solvent is a lower alkanol.

2. A method for preparing an adjuvant formulation having enhanced immunogenic activity, comprising:

(a) dissolving a selected quaternary ammonium salt in an oil component at a temperature of at least about 70° C., the salt having the structural formula

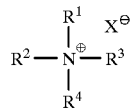

wherein $R^1$ and $R^2$ are independently selected from the group consisting of saturated hydrocarbon chains containing at least twelve carbon atoms, $R^3$ and $R^4$ are independently selected from lower alkyl groups, either unsubstituted or substituted with one to four substituents selected from the group consisting of hydroxyl and primary amino, and X is a halogen atom;

(b) admixing into the solution produced in step (a) an effective amount of a selected emulsifier; and (c) incorporating into the solution a biological buffer effective to provide the adjuvant formulation with a pH in the physiological range, wherein the relative quantities of quaternary ammonium salt, emulsifier, oil component and buffer are such that the adjuvant formulation contains approximately 5 to 15 mg quaternary ammonium salt in 1 ml formulation, the oil component represents approximately 10% to 60% by volume of the formulation, and the emulsifier represents approximately 0.5% to 1.5% by volume of the formulation.

3. An adjuvant formulation having enhanced immunogenic activity, comprising an admixture formed from a salt solution, an oil component, an emulsifier, and a biological buffer, wherein:

(a) the salt solution comprises a selected quaternary ammonium salt dissolved in a compatible solvent, the salt having the structural formula

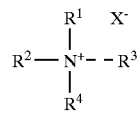

wherein $R^1$ and $R^2$ are independently selected from the group consisting of saturated hydrocarbon chains containing at least twelve carbon atoms, $R^3$ and $R^4$ are independently selected from lower alkyl groups, either unsubstituted or substituted with one to four substituents selected from the group consisting of hydroxyl and primary amino, and X is a halogen atom;

(b) the oil component is selected from the group consisting of a mineral oil, a vegetable oil, an animal oil, and mixtures thereof; and (c) the biological buffer provides the adjuvant formulation with a pH in the physiological range, wherein the relative quantities of quaternary ammonium salt, solvent, oil component, emulsifier, and buffer are such that the adjuvant formulation contains approximately 5 to 15 mg quaternary ammonium salt in 1 ml formulation, the oil component represents approximately 10% to 60% by volume of the formulation, the solvent represents approximately 5% to 15% by volume of the formulation, and the emulsifier represents approximately 0.5% to 1.5% by volume of the formulation, wherein the solvent is a lower alkanol, and further wherein the adjuvant formulation is prepared by the method of claim 1.

4. An adjuvant formulation having enhanced immunogenic activity, comprising an admixture formed from an oil phase, an emulsifier, and a biological buffer, wherein:

(a) the oil phase comprises a salt-in-oil solution having a selected quaternary ammonium salt dissolved in an oil component, the salt having the structural formula

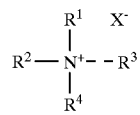

wherein $R^1$ and $R^2$ are independently selected from the group consisting of saturated hydrocarbon chains containing at least twelve carbon atoms, $R^3$ and $R^4$ are independently selected from lower alkyl groups, either unsubstituted or substituted with one to four substituents selected from the group consisting of hydroxyl and primary amino, and X is a halogen atom; and (b) the biological buffer provides the adjuvant formulation with a pH in the physiological range, wherein the relative quantities of quaternary ammonium salt, emulsifier, oil component and buffer are such that the adjuvant formulation contains approximately 5 to 15 mg quaternary ammonium salt in 1 ml formulation, the oil component represents approximately 10% to 60% by volume of the formulation, and the emulsifier represents approximately 0.5% to 1.5% by volume of the formulation, and further wherein the adjuvant formulation is prepared by the method of claim 1.

5. The adjuvant formulation of claim 3, wherein $R^1$ and $R^2$ are alkyl of twelve to twenty carbon atoms, and $R^3$ and $R^4$ are lower alkyl.

6. The adjuvant formulation of claim 5, wherein $R^1$ and $R^2$ are —$C_{18}H_{37}$ and $R^3$ and $R^4$ are methyl.

7. The adjuvant formulation of claim 5, wherein X is Br.

8. The adjuvant formulation of claim 4, wherein $R^1$ and $R^2$ are alkyl of twelve to twenty carbon atoms, and $R^3$ and $R^4$ are lower alkyl.

9. The adjuvant formulation of claim 8, wherein $R^1$ and $R^2$ are —$C_{18}H_{37}$ and $R^3$ and $R^4$ are methyl.

10. The adjuvant formulation of claim 8, wherein X is Br.

11. The adjuvant formulation of claim 4, wherein the oil is a mineral oil.

12. An immunogenic composition comprising the adjuvant formulation of claim 3 and a bacterial or viral antigen.

13. An immunogenic composition comprising the adjuvant formulation of claim 4 and a bacterial or viral antigen.

14. The immunogenic composition of claim 12, wherein the antigen is derived from a Pasteurella, Actinobacillus or Haemophilus species.

15. The immunogenic composition of claim 13, wherein the antigen is derived from a Pasteurella, Actinobacillus or Haemophilus species.

16. The immunogenic composition of claim 12, wherein the antigen is derived from a virus selected from the group consisting of Rotaviruses, Herpes viruses, Corona viruses, Respiratory Syncytial virus, Parainfluenza virus, Adenovirus, Pox viruses, and Bovine viral diarrhea viruses.

17. The immunogenic composition of claim 16, wherein the antigen is derived from Bovine herpes virus Type 1 (BHV-1).

18. The immunogenic composition of claim 16, wherein the antigen comprises BHV-1 gIV Antigen, or fragments thereof.

19. The immunogenic composition of claim 13, wherein the antigen is derived from a virus selected from the group consisting of Rotaviruses, Herpes viruses, Corona viruses, Respiratory Syncytial virus, Parainfluenza virus, Adenovirus, Pox viruses, and Bovine viral diarrhea viruses.

20. The immunogenic composition of claim 19, wherein the antigen is derived from Bovine herpes virus Type 1 (BHV-1).

21. The immunogenic composition of claim 20, wherein the antigen comprises BHV-1 gIV Antigen, or fragments thereof.

22. A immunogenic composition for DNA immunization comprising the adjuvant formulation of claim 3 and a DNA sequence encoding an antigen derived from a virus selected from the group consisting of Rotaviruses, Herpes viruses, Corona viruses, Respiratory Syncytial viruses, Parainfluenza viruses, Adenoviruses, Pox viruses, and Bovine viral diarrhea viruses.

23. A immunogenic composition for DNA immunization comprising the adjuvant formulation of claim 4 and a DNA sequence encoding an antigen derived from a virus selected from the group consisting of Rotaviruses, Herpes viruses, Corona viruses, Respiratory Syncytial viruses, Parainfluenza viruses, Adenoviruses, Pox viruses, and Bovine viral diarrhea viruses.

24. A method for inducing an enhanced immune response in a vertebrate subject, comprising administering to said vertebrate subject an immunogenic composition containing the adjuvant formulation of claim 3 and an antigen derived from a virus selected from the group consisting of Rotaviruses, Herpes viruses, Corona viruses, Respiratory Syncytial viruses, Parainfluenza viruses, Adenoviruses, Pox viruses, and Bovine viral diarrhea viruses.

25. A method for inducing an enhanced immune response in a vertebrate subject, comprising administering to said vertebrate subject an immunogenic composition containing the adjuvant formulation of claim 4 and an antigen derived from a virus selected from the group consisting of Rotaviruses, Herpes viruses, Corona viruses, Respiratory Syncytial viruses, Parainfluenza viruses, Adenoviruses, Pox viruses, and Bovine viral diarrhea viruses.

* * * * *